United States Patent [19]

Williams

[11] Patent Number: Plant 5,671

[45] Date of Patent: Feb. 25, 1986

[54] MINIATURE ROSE PLANT 'MINKCO'

[76] Inventor: Ernest D. Williams, 1510 Lebanon Ave., Dallas, Tex. 75208

[21] Appl. No.: 606,396

[22] Filed: May 2, 1984

[51] Int. Cl.[4] ..... A01H 5/00

[52] U.S. Cl. ..... Plt./10

[58] Field of Search ..... Plt./10

*Primary Examiner*—James R. Feyrer

[57] ABSTRACT

The subject of the present disclosure is a new and distinct variety of miniature rose plant characterized by the dark red color of the buds and flowers.

1 Drawing Figure

1

The present invention relates to a new and distinct variety of hardy, dwarf, bush type rose plant of the miniature class; the variety being primarily characterized—as to novelty—by the deep red color of buds and flowers which in general color effect are similar to Red Pinocchio, Floribunda (U.S. Plant Patent No. 812, expired).

The variety is further characterized by:

An abundance of bloom, with flowers borne singly (occasionally several) to the stem.

Slight fragrance.

A plant which is vigorous, of upright, bushy shape with semi-glossy (to matt) small foliage with pointed leaflets; the buds and flowers being similar in form and size to Over The Rainbow (miniature—U.S. Plant Pat. No. 3,472).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Tom Brown (floribunda—not patented) as the seed parent and Over The Rainbow (miniature—U.S. Plant Pat. No. 3,472) as the pollen parent.

Subsequent to origination of the variety I successfully asexually reproduced it at my nursery, located as aforesaid, by cuttings; the reproductions having run true in all respects.

The color photograph illustrates the variety, including the foliage, buds and flowers.

Referring now sepcifically to the new and distinct variety of miniature rose plant, the following is a detailed description thereof in outline; all major color plate identifications being by reference to The British Colour Council Horticultural Chart, except where common terms of color definition are employed.

Type: Hardy; dwarf; bushy; upright; seedlings; greenhouse; outdoors; cut flowers; garden decoration; potted plant.

Class: Miniature.

*Variety name.*—Minkco (Var: Black Jack).

Fowers borne: Singly (occasionally several on slender, wirey stems.

Quantity of bloom: Abundant both outside and in greenhouse.

2

Bud:

*Peduncle.*—Medium to long; slender but sturdy; erect; medium to light green; hairs — few or none. Before calyx breaks; size — small. Form long: pointed with several foliaceous apendages on surface of bud; with foliaceous parts extending beyond the tip of the bud equal to one-half or more of its length.

*Color.*—Medium green.

*As calyx breaks, color.*—Dark (blackish) red. Opening: opens well in all weather.

Bloom:

*Size when fully open.*—Small, averaging about $1\frac{1}{4}$–$1\frac{1}{2}$".

*Petalage.*—Averaging about 40 petals, arranged regularly.

*Form.*—High centered with petals rolled loosely outward, and later at maturity full and somewhat rounded. Open flowers may show stamens.

Petals: Fairly thick; velvety on inside and satiny on outside surface.

*Shape.*—Outside petals, broad lanceolate (nearly round) with acute tip; intermediate — broad lanceolate with short acute tip; inside — lanceolate with acute or rounded tip.

Color: Newly opened flower from a plant grown outdoors;

*Outside petal.*—Outside surface — dark red — near Chrysanthemum Crimson 824 to Indian Lake 828 becoming lighter near base with small yellowish area at base. Inside surface — near Indian Lake 828 blending into lighter shade then into yellow at base.

*Intermediate petal.*—Outside surface — similar to outside petal. Inside surface — similar to but tending to be lighter shade than outside petal.

*Inner petal.*—Outside surface — same as intermediate petal; inside surface — same as intermediate petal. General color effect; newly opened flowers — color: dark red. Three days open — Color similar to newly opened flowers but slightly lighter color. Behavior — Opens well in all weather. Spent petals drop off. Flower longevity (May 1983) — Plant in pot 6–8 days. Cut flowers at living room temperature 4–6 days.

Reproductive organs:

*Stamens.*—Several to numerous, arranged regularly about pistils.

*Filaments.*—Varying length, medium to long, yellow.

*Anthers.*—Yellow.

*Pollen.*—Fair amount.
*Pistils.*—Average number.
*Ovaries.*—All enclosed in calyx.
*Hips.*—Numerous — round to oval shape.
*Sepals.*—Permanent; spear shape; recurved.
*Seed.*—Several.

Foliage:

*Leaves.*—Compound of five (sometimes seven) leaflets — small; leather; semi-glossy to matt.
*Leaflets.*—Shape: broad lanceolate; nearly oval; apex acute; base rounded or rounded acute. Margin: Serrate. Color: Deep green; new growth — reddish to bronze. Rachis: Medium strength; upper side may have a few tiny short hairs. Stipules: Medium long; narrow to medium width; short length narrow points which turn out usually at about 45 degrees.

Growth:

*Habit.*—Dwarf; bushy; upright; much branched.
*Growth.*—Free; vigorous; internodes short.
*Canes.*—Medium; slender; sturdy.
*Main stems.*—Color: medium green.

*Thorns.*—Average number; small; slender. Prickles — Few or none. Hairs — None.
*Branches.* —Color: light to medium green. Thorns: few; small; slender. Medium to short oval base. Prickles: none. Hairs: usually none.
*Young shoots.*—Color: bronze or reddish. Thorns: average number.

The miniature rose plant and its flowers as herein described may vary in slight detail due to climatic, soil and cultural conditions under which the variety may be grown; the present description being of the variety as grown at Dallas, Tex., and at Visalia, Calif.

The following is claimed:

1. A new and distinct variety of miniature rose plant of hardy, dwarf, bushy, rounded, much branched habit, substantially as illustrated and described, characterized by buds and flowers which are of a deep red color, often with blackish shading, with pointed buds of good substance suitable for cutting and exhibition,; and further characterized by a plant which is easy to propagate from soft wood cuttings, with an abundance of flowers usually borne singly on slender wirey stems.

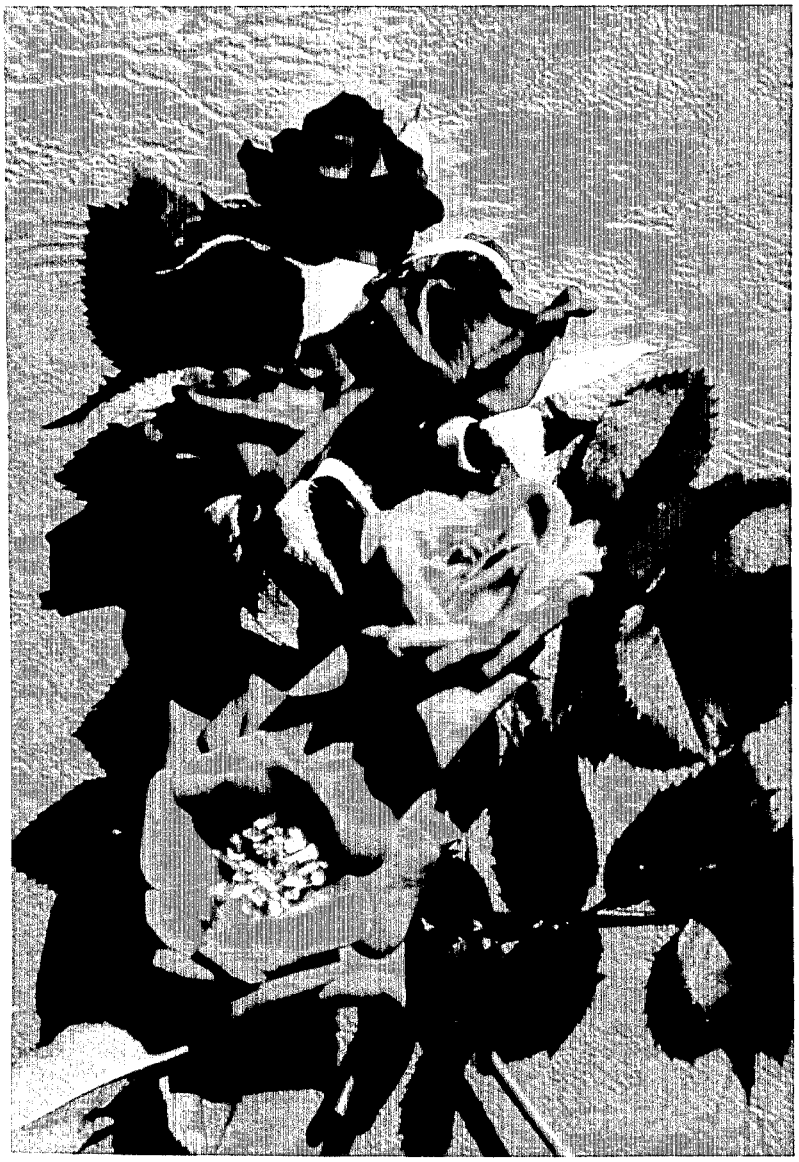

* * * * *